Figure 1:
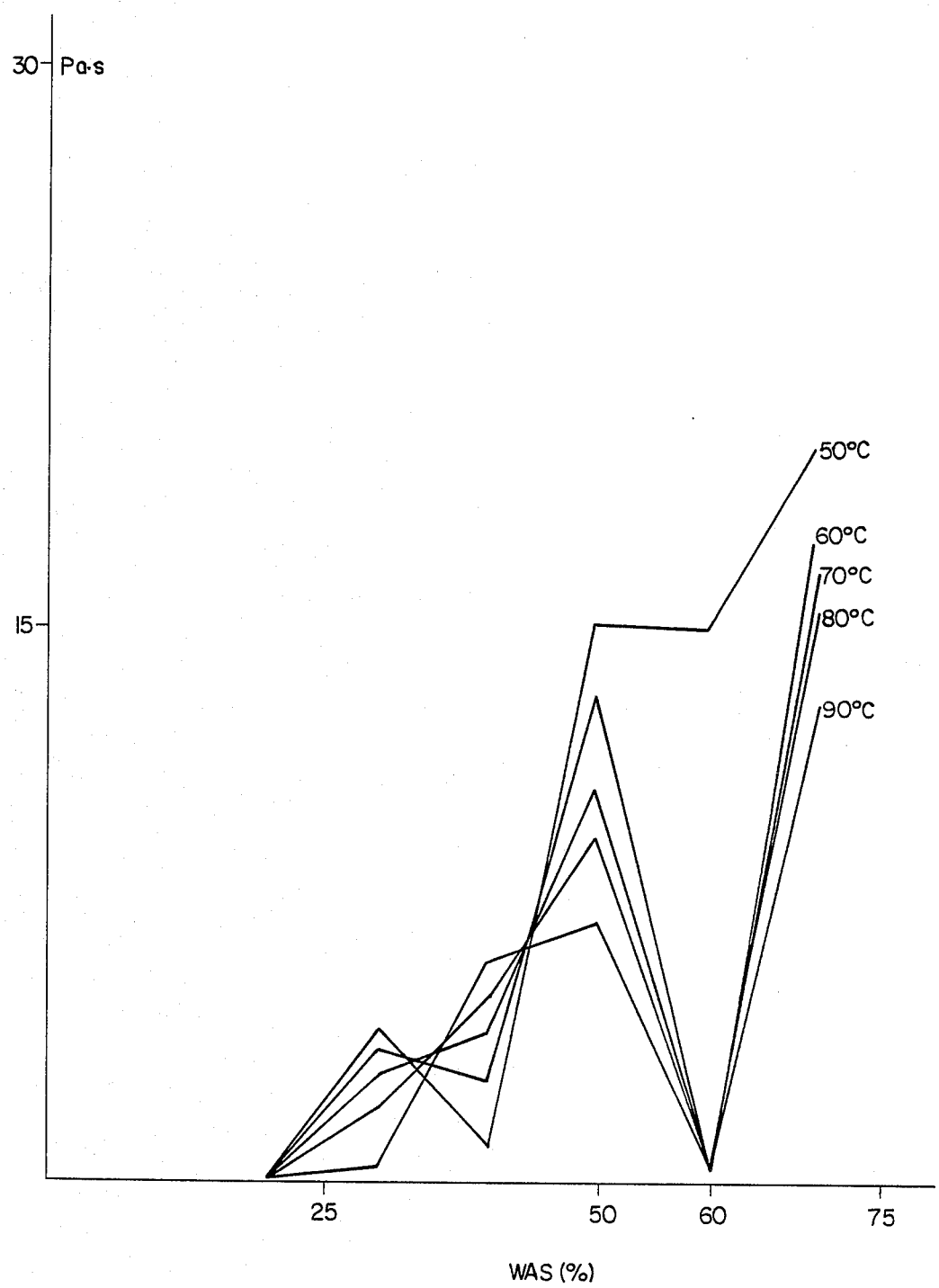

United States Patent [19]

Piorr et al.

[11] Patent Number: 4,820,451
[45] Date of Patent: Apr. 11, 1989

[54] PROCESS FOR THE PRODUCTION OF MOBILE PASTES OF WASHING-ACTIVE α-SULFOFATTY ACID ESTER SALTS OF HIGH SOLIDS CONTENT

[75] Inventors: Robert Piorr, Ratingen-Hoesel; Hans-Josef Rommerskirchen; Horst Ritterbex, both of Duesseldorf; Frantisek Jost, Duesseldorf, all of Fed. Rep. of Germany

[73] Assignee: Henkel Kommanditgesellschaft auf Aktien, Duesseldorf, Fed. Rep. of Germany

[21] Appl. No.: 925,442

[22] Filed: Oct. 31, 1986

[30] Foreign Application Priority Data

Nov. 2, 1985 [DE] Fed. Rep. of Germany ....... 3538910

[51] Int. Cl.$^4$ ........................................... C07F 143/90
[52] U.S. Cl. ...................................................... 260/400
[58] Field of Search ........................................ 260/400

[56] References Cited

U.S. PATENT DOCUMENTS

| 3,142,691 | 7/1964 | Wulff et al. | 260/400 |
| 3,158,632 | 11/1964 | Blaser et al. | 260/400 |
| 3,159,657 | 12/1964 | Wulff et al. | 260/400 |
| 3,251,868 | 5/1966 | Stein et al. | 260/400 |
| 3,256,303 | 6/1966 | Stein et al. | 260/400 |
| 3,354,187 | 11/1967 | Stein et al. | 260/400 |
| 3,452,064 | 6/1969 | Stein et al. | 260/400 |
| 4,404,143 | 9/1983 | Sekiguchi et al. | 260/400 |
| 4,495,092 | 1/1985 | Schmid et al. | 252/559 |
| 4,668,438 | 5/1987 | Piorr et al. | 260/400 |
| 4,695,409 | 9/1987 | Piorr et al. | 260/400 |

FOREIGN PATENT DOCUMENTS 3334517  4/1984  Fed. Rep. of Germany .

Primary Examiner—Anton H. Sutto
Attorney, Agent, or Firm—Ernest G. Szoke; Wayne C. Jaeschke; Real J. Grandmaison

[57] ABSTRACT

In the production of washing-active α-sulfofatty acid esters by sulfonation of fatty acid alkyl esters with $SO_3$ in molar ratios of up to 1:2 and more especially of from 1:1.2 to 1:1.8 and subsequent working-up of the crude sulfonic acid in aqueous medium with salt formation, aqueous pastes which are mobile, more especially pumpable, at moderately elevated temperatures are obtained by subjecting the crude sulfonate before the treatment with the aqueous medium to a post-reaction with at least about 0.5 mole equivalent, based on the $SO_3$ which is not used for the α-sulfonation, of monohydric alcohols and/or alkoxylation products thereof at temperatures above 70° C. and adjusting the solids contents of the α-sulfofatty acid ester salts to more than 35% by weight in the subsequent aqueous working-up step.

20 Claims, 3 Drawing Sheets

PROCESS FOR THE PRODUCTION OF MOBILE PASTES OF WASHING-ACTIVE α-SULFOFATTY ACID ESTER SALTS OF HIGH SOLIDS CONTENT

BACKGROUND OF THE INVENTION

1. Field of the Invention

This invention relates to aqueous slurries of ester sulfonates having desirable viscosity and concentration properties, and more particularly, to the method of preparing such ester sulfonates.

It is known that α-sulfofatty acid ester salts can be obtained in the form of aqueous pastes by neutralization of α-sulfofatty acid esters with alkali metal hydroxide, particularly aqueous alkali metal hydroxide. The starting materials used on an industrial scale are fatty acid esters which are obtained from fats and/or oils of natural origin by ester cleavage and subsequent esterification with lower alkanols, particularly methanol, or by transesterification of the natural triglycerides with the lower alkanols. Depending on the orgin of the natural raw material, the fatty acid ester mixtures obtained contain fatty acids of a compartively broad range which is normally covered by $C_{10}-C_{24}$. The sulfonation of these fatty acid ester mixtures, particularly with gaseous $SO_3$, leads to more or less heavily discolored crude sulfonic acids which have to be bleached and converted into ester sulfonate pastes by neutralization to a pH value of from about 6 to 7. In this form, they are now becoming increasingly important in practice as surfactants or wetting agents for detergents and cleaning preparations containing renewable raw materials of natural origin.

Pastes of the type in question of alkali metal salts of α-sulfonated fatty acid alkylesters, hereinafter referred to as ester sulfonate salts, are particularly difficult to handle on an industrial scale because of their concentration and viscosity behavior. In aqueous admixture, the ester sulfonate salts obtained on an industrial scale only form sufficiently mobile solutions or suspensions assuring the uninterrupted completion of technical processes at comparatively low solids concentrations, for example, at solids contents of up to about 35% by weight. With higher ester sulfonate salt contents, for example, solids contents of about 40% by weight or higher, the viscosity of the aqueous preparation increases to such an extent that it no longer shows free mobility. This results in serious limitations. Thus, attempts to directly obtain highly concentratd ester sulfonate salts pastes by neutralization of the crude sulfonic acid mixture with concentrated alkali metal hydroxide solution fail because both the stirrability and hence the uniform miscibility of the reaction mixture are lost. At the same time, this makes it impossible to dissipate the heat of neutralization. Undesirable secondary reactions, more especially undesirably heavy formation of disalts of the -sulfofatty acids with ester cleavage, occur through local concentration and temperature peaks.

The above-mentioned disalts of the α-sulfofatty acids are undesirable for several reasons. They have only limited solubility in water and, in addition, show poor surface activities. Above all, however, they also affect the viscosity of the aqueous ester sulfonate pastes. An excessively high content leads to a considerable increase in the viscosity of the aqueous ester sulfonate pastes. Understandably, ester sulfonate pastes immobilized through an increase in viscosity can no longer be pumped in a large-scale operation. This results in the blockage of pipes and hence in persistent interference with the operation of the plant as a whole.

2. Description of Related Art

The state of the art relating to ester sulfonate salt pastes of the type in question is greatly concerned with these problems. In particular, it has been proposed to use flow aids or viscosity regulators with a view to improving the flow behavior of aqueous technical concentrates of α-sulfofatty acid ester salts. Thus, U.S. Pat. No. 4,495,092, for example, describes the use as viscosity regulators of $C_8-C_{40}$ alcohols which, in addition, may contain one or more hydroxyl groups as substituents and onto which up to 20 moles of ethylene oxide and/or propylene oxide per mole of alkanol may be added. These viscosity regulators are added to the aqueous ester sulfonate paste in quantities of from 1 to 15% by weight, based on the quantity of surfactant, adjusting the viscosity of the surfactant concentrate to a value of at most 10,000 mPa.s at 70° C.

In recent years, special attention has been devoted to this particular aspect of the prodcution of surfactants based on ester sulfonates which, generally, involves numerous difficulties. Reference is made in this connection to DE-OS No. 31 23 681 and to DE-OS No. 33 34 517. According to DE-OS No. 31 23 681, a highly concentrated aqueous solution of a salt of α-sulfofatty acid esters may be prepared by neutralization of the sulfonated fatty acid product with an aqueous alkali metal solution in two stages. In the first stage, the sulfonated fatty acid product is neutralized with an aqueous alkali metal solution of relatively high concentration (15 to 50% by weight alkali metal) in the presence of a $C_1-C_4$ alcohol in a quantity of from 5 to 20% by weight, based on the weight of the sulfonated product, to a pH value of from 2.5 to 4, followed by a second stage of neutralization to a final pH of from 6 to 7 using a relatively highly diluted aqueous alkali metal solution. The crude sulfonation product may even be bleached before the two-stage neutralization treatment. In this regard, it is preferred to use an aqueous solution of $H_2O_2$, again in the presence of a $C_1-C_4$ alcohol. The hydrogen peroxide is reported to be used in the form of an aqueous solution having a concentration of 10% by weight or higher. The preferred alcohol is methanol where the fatty acid esters are methylesters. According to DE-OS No. 31 23 681, it is said to be possible to reduce the disalt content of the corresponding α-sulfofatty acids to 5% or lower.

However, DE-OS No. 33 34 517 then describes the disadvantages of the aforementioned proposal. The sulfonation products contain the short-chain alcohol used in considerably excessive large quantities in the aqueous neutralized reaction product. This is undesirable in that the short-chain alcohol interferes with the production of detergent mixtures by spray drying; in particular, it initiates undesirable pluming in the spray tower. In addition, the free alcohols present in the surfactant mixture have an undesirable foreign odor so that deodorization is necessary. To solve these various problems, DE-OS No. 33 34 517 proposes carrying out the aqueous bleaching and the neutralization of the crude α-sulfofatty acid esters in the presence of such quantities of a lower alcohol that an aqueous suspension containing from 30 to 55% by weight of the α-sulfofatty acid ester salt and, based on the weight of the α-sulfofatty acid ester salt, from 5 to 15% by weight of a lower alcohol sulfate and from 8 to 40% by weight of the lower alcohol is obtained. Finally, the aqueous suspension is said to be concentrated to such an extent that it contains from 40 to 65% by weight of α-sulfofatty acid ester salt, from 2 to 10% by weight of a lower alcohol sulfate and, optionally, at most 2% by weight of a lower alcohol.

The teaching of earlier German Patent Application No. P 34 32 324.4 is based on the surprising observation that the undesirable formation of α-sulfofatty acid disalts can be prevented by a much more practical method. There is no longer any need to use large excesses of alcohol, which in turn eliminates the need for the optional subsequent concentration by evaporation to eliminate unwanted alcohol fractions. The process is based on the finding that a carefully controlled treatment of the crude sulfonic acid of fatty acid alkylesters with any alcohols in small quantities defined hereinafter leads to a controllable reduction in the content of unwanted disalt, providing the post-reaction is carried out before any subsequent treatment with aqueous media. Another important precondition for the desired course of the post-reaction is a sufficiently high reaction temperature which is preferably above 60° C. and more especially above 75° C. The post-reaction of the crude sulfonic acid with alcohols before any introduction of water into the reaction mixture results, inter alia, in the formation of esters of the α-sulfonated fatty acids with the alcohols subsequently introduced into the reaction mixture. The reaction product may thus be described as a partially transesterified mixture of α-sulfofatty acid esters which, after its aqueous working up, ultimately contains other components, including, inter alia, limited quantities of alcohol sulfates.

3. Description of the Invention

The teaching of the present invention is based on the surprising finding that, after working up and conversion into ester sufonate salt pastes, reaction mixtures according to the aforementioned earlier patent application are capable of showing particularly desirable concentration and viscosity behavior. It has surprisingly been found that it is possible by means of the post-reaction described above ultimately to prepare ester sulfonate pastes of low disalt content which, despite solids contents above 35% by weight and, more especially, in the range of from about 40 to 65% by weight of washing-active substance in aqueous solution or suspension, provide mixtures which are mobile and in particular pumpable even at only moderately elevated temperatures.

Other than in the operating examples, or where otherwise indicated, all numbers expressing quantities of ingredients or reaction conditions used herein are to be understood as modified in all instances by the term "about".

In accordance with this invention, the particular alcohol component used for the post-reaction influences this viscosity/concentration behavior so that it is possible to prepare highly concentrated free-flowing solutions or pastes of aqueous ester sulfonate salts which may be transported, for example, in tanker lorries and processed therefrom.

In a preferred embodiment, therefore, the present invention relates to a process for the production of aqueous pastes of washing-active α-sulfofatty acid ester salts which, despite their high solids contents, are mobile and, in particular, are pumpable even at only moderately elevated temperatures. The α-sulfofatty acid ester salts are obtained by sulfonation of fatty acid alkylesters with $SO_3$ in molar ratios of up to 1:2 and more especially of from 1:1.2 to 1:1.8 and subsequent working up of the crude sulfonic acid in aqueous medium with salt formation, characterized in that, before the treatment with an aqueous medium, the crude sulfonic acid is subjected to a post-reaction with at least about 0.5 mole equivalent, based on the $SO_3$ which is not used for the α-sulfonation, of monohydric alcohols and/or alkoxylation products thereof at temperatures above 70° C. and in that the solids contents of the α-sulfofatty acid ester salts above 35% by weight are adjusted in the following aqueous working-up step.

The solids contents of the ester sulfonate salt pastes prepared in accordance with this invention and, in particular, the content of the resulting ester mixture of the α-sulfonated fatty acids is preferably in the range of from about 40 to 65% by weight.

Alkanols or alkoxylation products thereof containing up to 30 carbon atoms in the alcohol function (in the case of the corresponding alkoxylation products, preferably up to 20 alkoxy groups may be present in the molecule) are particularly suitable for the post-reaction of the crude sulfonic acid before its treatment with aqueous media. Accordingly, hydroxyl-containing components containing from 2 to 22 carbon atoms in the alcohol component are particularly suitable. In addition, it is preferred, where alkoxylation products of these alcohols are used, to employ corresponding compounds containing at least some and preferably at least 50% by weight ethylene oxide groups, i.e., groups having the structure $-CH_2CH_2O-$. In addition to or, if desired, even in place of such ethylene oxide groups, corresponding groups derived from propylene oxide may be present in known manner.

One particularly interesting class of compounds for adjusting the favorable viscosity/concentration behavior required in accordance with this invention comprises alkoxylation products of lower alcohols containing in particular up to 6 carbon atoms, and preferably from 2 to 4 carbon atoms, in the alcohol molecule. Alkoxylation products such as these may contain, for example, from 2 to 15, and preferably from 5 to 12, ethylene oxide units in the alkylene glycolether group. Accordingly, the ethoxylated alcohol component used for the post-reaction is sufficiently high-boiling as such, so that any residues of this component remaining in the reaction mixture do not interfere with the further working-up of the ester sulfonate salts. In addition, these components are also particularly effective in reducing the viscosity of highly concentrated aqueous ester sulfonate pastes. For example, the post-reaction of the crude sulfonic acid with an ethanol/10 mole ethylene oxide condensate may provide aqueous solutions which, even with solids contents of 60% by weight and higher, are comparatively low viscosity solutions at temperatures of, for example, from 40 to 60° C. and, accordingly, are suitable for problem-free transport in tanker lorries.

However, the use of typical fatty alcohols, i.e., alcohols containing from about 10 to 20 carbon atoms, and/or alkoxylation products thereof also leads to mobile pastes which are still pumpable, for example, at solids contents of around 60% by weight and at temperatures of from 50° to 60° C.

One particular characteristic of the ester sulfonate pastes prepared in accordance with this invention is that the desired favorable viscosity/concentration behavior remains substantially intact over the entire concentration range of from about 35 to 65% by weight solids. This represents a major difference from the fatty acid methylester sulfonate salts prepared without the alcoholic post-reaction according to this invention. Earlier Patent Application No. P 34 39 520.2, which has not yet been published, describes pastes of alkali salts of α-sulfonated fatty acid alkylesters which are aqueous at temperatures of at least 60° C. These pastes have ester sulfonate salt solids contents of at least about 60% by weight and are substantially free from viscosity regulators. However, the limitation of the fatty acid base to $C_{16}$ and/or $C_{18}$ fatty acids is essential therein. It is only where such fatty acids are used that the desired reduction in viscosity is achieved at very high solids contents of the ester sulfonate pastes of around 60 to 70% by weight. With lower concentrations of corresponding ester sulfonates, particularly in the range of from 40 to 55% by weight, the corresponding aqueous suspensions pass through highly viscous phases so that difficult and relatively complicated process steps have to be negotiated in the continuous production of the highly concentrated ester sulfonate pastes (cf. the disclosure of the earlier Patent Application mentioned above).

By contrast, the products subjected to the alcoholic post-reaction according to this invention may be moved without difficulty and are therefore easy to process evenly and precisely in the critical concentration range of from about 35 to 60% by weight solids.

The particular process conditions under which the post-reaction is carried out largely correspond to the disclosure of the earlier Patent Application mentioned above, i.e., German Patent Application No. 34 32 324.4.

One preferred embodiment of the process according to this invention is characterized by the limitation of the content of free alcohol in the reaction product. Accordingly, no more than about 2 mole equivalents of the free alcohol component are used in the transesterification stage. More preferably, no more than about 1.5 mole equivalents of the alcohol are used in this stage. The mole equivalents are again based on the $SO_3$ in the crude sulfonation product which was not used for the α-sulfonation. Accordingly, this $SO_3$ reference basis is the sum of two partial amounts. One of these partial amounts corresponds to the $SO_3$ excess which was used in the sulfonation step, to increase the conversion, over and above the quantity of $SO_3$ required for the α-sulfonation. The other partial amount is the difference between the quantity of $SO_3$ theoretically required and the amount actually consumed in the α-sulfonation step.

In general, it is best to use quantities of no more than about 1.3 mole equivalents of the alcohol, based on the quantity of $SO_3$ explained above. The alcohol is preferably used in quantities of from 0.8 to 1.3 mole equivalents and more preferably in quantities of from 0.9 to 1.1 mole equivalents.

The conditions for the esterification reaction are selected, particularly with the reactivity of the alcohol used for transesterification in mind, in such a way as to minimize the additional thermal load on the reaction mixture. It is possible in this way to limit or prevent the formation of any undesirable additional discoloration in the reaction product. However, sufficiently intensive reaction conditions are necessary to bring about the transesterification required in accordance with this invention. In general, the post-reaction is carried out at temperatures no higher than 150° C. and preferably at temperatures no higher than 120° C. Temperatures above 75° C. can be particularly suitable. A suitable temperature range is, for example, for 75° to 100° C.

The reaction time is determined in dependence upon the reactivity of the alcohol used for transesterification and upon the particular reaction temperature selected. In general, a reaction time of at least 5 minutes and, more especially, at least 10 minutes will be necessary, a reaction time of from about 10 to 30 minutes normally being suitable.

More particulary, the post-reaction process conditions are selected on the basis of the following general principle: lower alcohols show comparatively high reactivity in the transesterification reaction. In general, higher alcohols show lower reactivity. Fatty or wax alcohols are mentioned as an example. Accordingly, their use requires more intensive reaction conditions within the parameters mentioned.

The reaction components and the process conditions are generally selected in such a way that the reaction product treated with aqueous media and neutralized contains less than 10% by weight, based on washing-active substance, of disalts. Disalt contents of or below 5% by weight are preferred, although it is possible to obtain even lower contents, for example of less than 2% by weight.

Generally speaking, the alcohols used for the transesterification—in a preferred embodiment—do not contain any reactive groups, apart from the hydroxyl group, in the molecule which are capable of undesirable secondary reactions.

Suitable alcohol components are, for example, monofunctional aliphatic and cycloaliphatic alcohols containing from 1 to 30 and preferably from 1 to 24 carbon atoms, such as methanol, ethanol, n-propanol, i-propanol, n-butanol, 2-butanol, n-pentanol, 2-pentanol, n-hexanol, n-octanol, n-decanol, n-dodecanol, n-tetradecanol, n-hexadecanol, n-octadecanol, n-eicosanol, n-docosanol, 2-hexydecanol, 2-octyldodecanol, 2-dodecylhexadecanol, oxoalcohols containing from 9 to 18 carbon atoms, Ziegler alcohols containing from 8 to 20 carbon atoms, cyclohexanol and methylcyclohexanols.

Other examples of possible alcohol components are glycol semiethers, such as methylethylene glycol, ethylethylene glycol and adducts of from 1 to 20 moles ethylene oxide and/or propylene oxide with $C_1$–$C_{24}$ aliphatic alcohols, more especially with fatty alcohols and fatty alcohol mixtures.

The alcohols mentioned may be used either individually or in admixture in the process according to this invention. Fatty alcohols in the narrower sense, i.e., straight-chain aliphatic alcohols containing from 8 to 24 carbon atoms, are generally used in the form of mixtures commensurate with their origin. The composition of alcohol mixtures such as these is determined by the natural fats and oils used as starting material for their production.

In a preferred embodiment of the process according to this invention, the crude sulfonic acid to be subjected to the transesterification should contain no more than 80 mole % and preferably no more than 50 mole % of $SO_3$ unused in the α- sulfonation, based in each case on the α-sulfofatty acid ester formed. In addition, this crude sulfonic acid preferably has a degree of sulfonation of at least 90%, more especially of at least 95% and, better yet, of 98% or higher, in each case on the fatty acid ester used.

The sulfonation preceding the transesterification step is carried out in accordance with the prior art as represented, for example, by U.S. Pat. Nos. 3,256,303 and 3,158,632. The starting materials preferably used for sulfonation are lower alkylesters, more especially the methylesters of fatty acids containing, for example, from 6 to 28 and preferably, from 8 to 18 carbon atoms. These fatty acid esters preferably originate from natural fats of plants, land or aquatic animals. Apart from the hydrogen atom in the α-position, they should not contain any other sulfatable or sulfonatable groups, particularly double bonds or alcoholic hydroxyl groups. Their iodine numbers should be below 5 and preferably below 2. The sulfonation is carried out with an $SO_3$/inert gas mixture, which may normally contain from 2 to 40% by volume $SO_3$, at temperatures of or not much higher than 100° C., and preferably 95° C. The sulfonation temperature may either be constant or may assume a stepped profile, as described in the aforementioned publications.

The post-reaction with alcohols according to this invention is followed by working up of the reaction product with aqueous media in known manner. The working-up step comprises in particular bleaching and neutralization of the crude sulfonic acid transesterified in accordance with this invention. Bleaching may be carried out in known manner with aqueous hydrogen peroxide and/or alkali metal hypochlorite solution. Neutralization may precede bleaching or may be carried out after bleaching. Acidic bleaching with hydrogen peroxide is described, for example in U.S. Pat. Nos. 3,142,691; 3,159,657; 3,251,868 and 3,354,187. A combined bleaching treatment in which acidic peroxide bleaching is followed by neutralization of the sulfonated and partially bleached material, in turn by a final bleaching treatment with hydrogen peroxide or, better yet, with hypochlorite, is described in U.S. Pat. No. 3,452,064.

The process conditions for the bleaching and/or neutralization step are selected in such a way that ester saponification, which is possible in principle, is prevented or suppressed as far as possible. Without these precautionary measures, the advantages of the transesterification step according to this invention in regard to reduction of the disalt content would be at least partially lost.

EXAMPLE 1

In a falling film reactor, 283 g. (1 mole) of hardened tallow fatty acid methylester (iodine number 0.5; saponification number 198) were sulfonated at 90° C. with 96 g. (1.2 moles) of sulfur trioxide (5% by volume in air). The resulting reaction mixture was then aged for 30 minutes at 90° C. The degree of sulfonation was 98%.

7.0 g. (0.22 mole) of methanol were added with stirring at 90° C. to the aged, crude sulfonation product, followed by stirring for another 20 minutes at 90° C. 16 g. of hydrogen peroxide in the form of a 35% by weight aqueous solution was then added to the reaction product for bleaching, followed by stirring for 10 minutes at 60° C. before the reaction product was neutralized to pH 7 by addition of 25% by weight sodium hydroxide solution.

Partial amounts of the concentrated α-sulfofatty acid ester salt solution obtained were adjusted to contents of washing-active substance of 30, 40, 50, 60 and 70% by weight. The apparent viscosities of the solutions obtained were measured at 50, 60, 70, 80 and 90° C. and at a shear velocity of 100 $s^{-1}$ using a rotational rheometer (Rheomat 30 in combination with measuring systems of the DIN 14 or DIN 25 type and an HP 85 data station; manufacturer: Contraves AG, Zurich, Switzerland). The data obtained are shown in the form of a graph in FIG. 1.

EXAMPLE 2

In a falling film reactor, 283 g. (1 mole) of hardened tallow fatty acid methylester (iodine number 0.5; saponification number 198) were sulfonated at 90° C. with 112 g. (1.4 moles) of sulfur trioxide (5% by volume in air). The reaction mixture thus obtained was aged for 20 minutes at 90° C. The degree of sulfonation was 98%.

214 g. (0.44 mole) of an adduct of 10 moles of ethylene oxide with ethanol were added with stirring at 90° C. to the aged, crude sulfonation product, followed by stirring for another 20 minutes at 90° C. The reaction product was then bleached with hydrogen peroxide and neutralized with sodium hydroxide solution in the same way as in Example 1.

Figure 2:
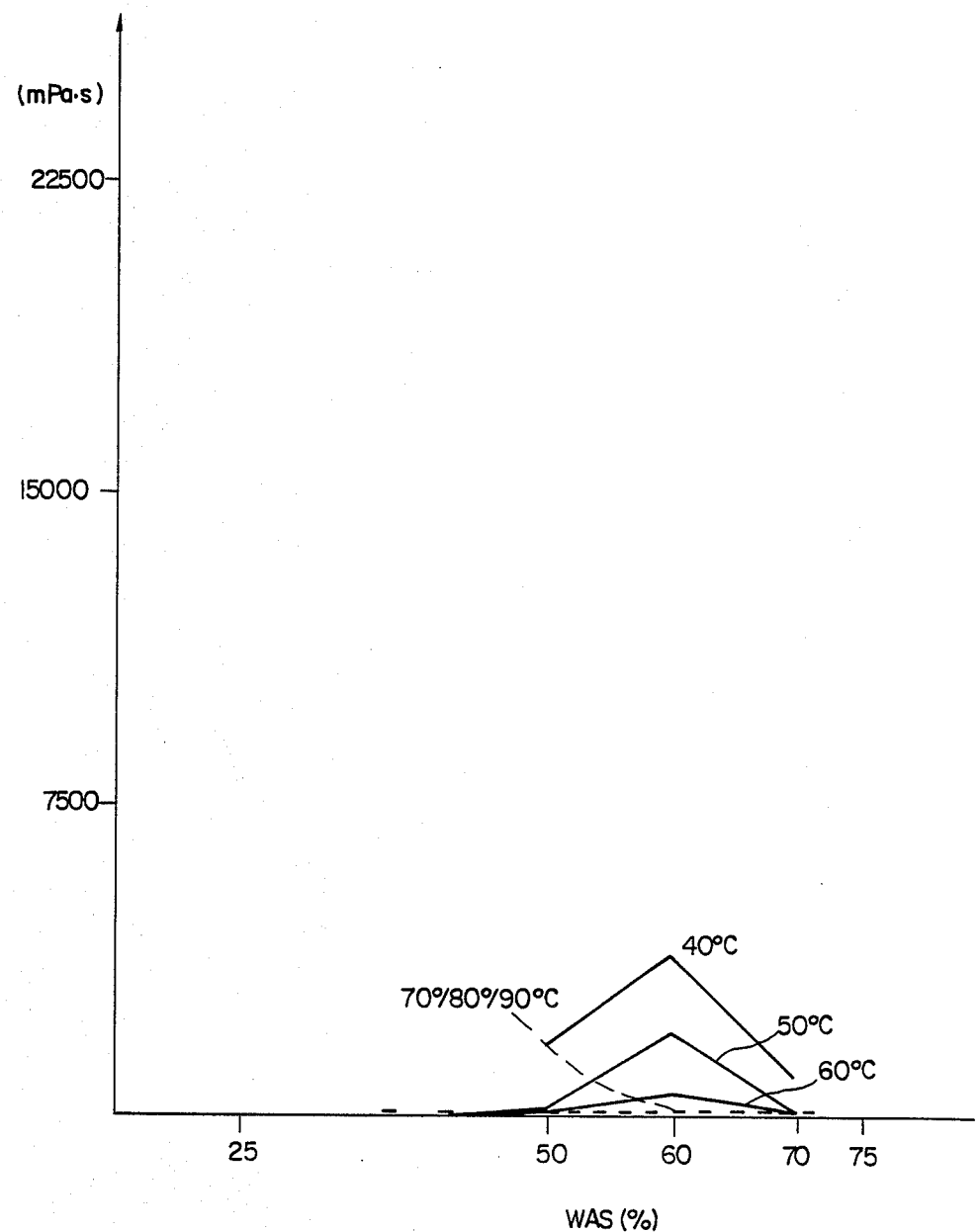

Partial amounts of the concentrated α-sulfofatty acid ester salt solution obtained were adjusted to contents of washing-active substance of 40, 50, 60 and 70% by weight. The apparent viscosities of these solutions were determined as described in Example 1 at 40°, 50°, 60°, 70°, 80° and 90° C. and at a shear velocity of 100 $s^{-1}$. The measured data are shown in the form of a graph in FIG. 2.

EXAMPLE 3

For comparison purposes, 283 g. (1 mole) of tallow fatty acid methylester (iodine number 0.5; saponification number 198) were sulfonated at 90° C. with 96 g. (1.2 moles) of sulfur trioxide (5% by volume in air). The reaction mixture was then aged for 30 minutes at 90° C. The degree of sulfonation was 98%.

Without preliminary reaction with an alcohol, the aged, crude sulfonation product was bleached and neutralized in the same way as in Example 1.

Figure 3:
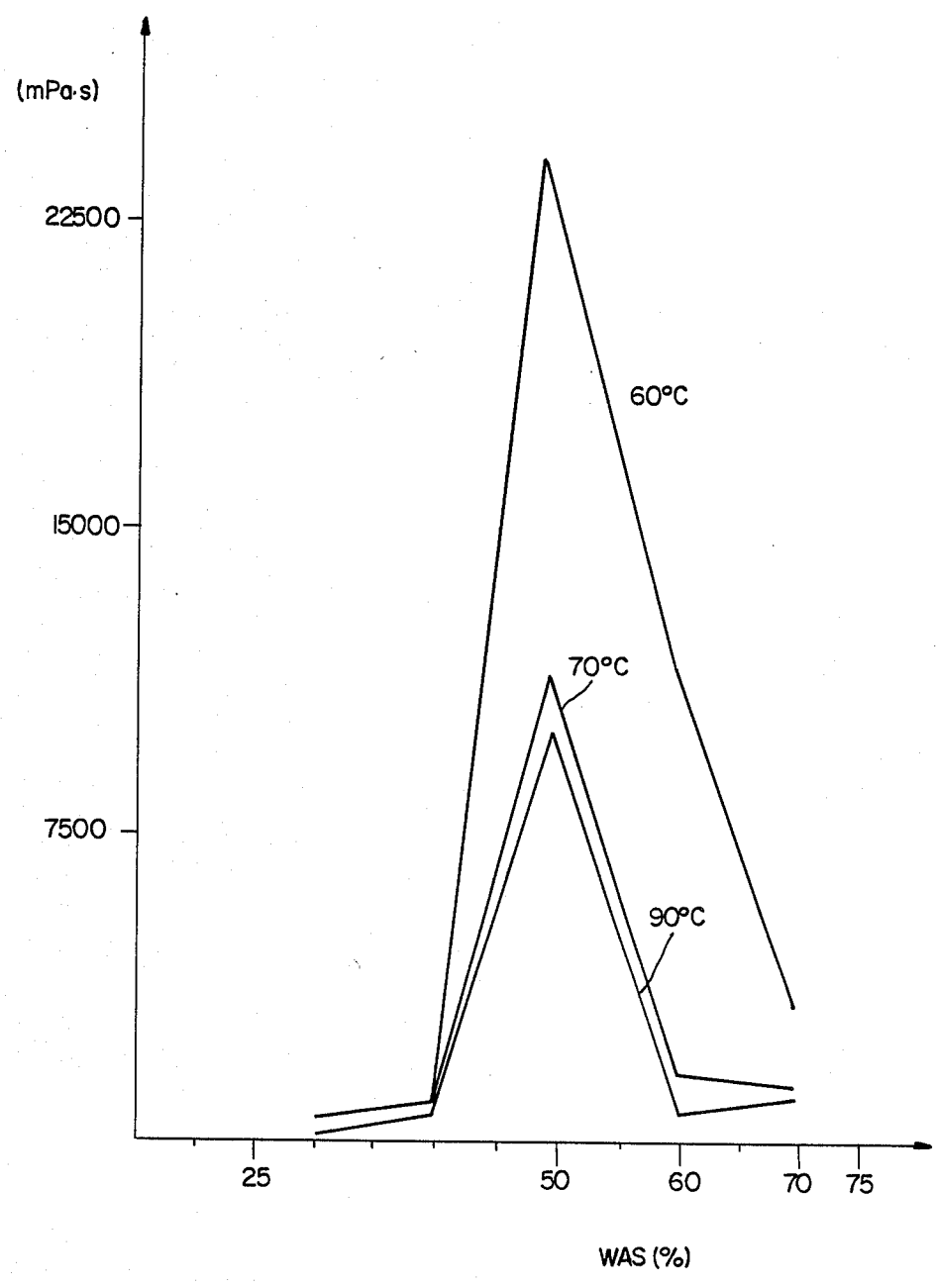

Partial amounts of the concentrated α-sulfofatty acid ester salt solution obtained were adjusted to contents of washing-active substance of 30, 40, 50, 60 and 70% by weight. The apparent viscosities of these solutions were determined as described in Example 1 at 60°, 70° and 90° C. and at a shear velocity of 100 $s^{-1}$. The measured data are shown in the form of a graph in FIG. 3.

We claim:

1. A process for the production of aqueous pastes of washing-active α-sulfofatty acid ester salts which, despite high solids contents, are mobile and, in particular, pumpable even at moderately elevated temperatures, said process comprising: (1) sulfonating fatty acid alkylesters with sulfur trioxide in molar ratios of up to 1:2 thereby producing crude sulfonic acid; (2) subjecting said sulfonic acid to a post-reaction with at least about 0.5 mole equivalent, based on the sulfur trioxide unused in the sulfonation, of monohydric alcohols and/or alkoxylation products thereof at temperatures above about 70° C.; (3) bleaching and neutralizing said crude sulfonic acid; and (4) working up the bleached and neutralized sulfonic acid to obtain α-sulfofatty acid ester salts in a solids content above 35% by weight.

2. A process in accordance with claim 1 wherein said post-reaction with said alcohols or alkoxylation products thereof is carried out at temperatures of from about 80° C. to about 100° C., and said alcohols or alkoxylation products thereof are employed in substantially equimolar quantities based on said sulfur trioxide unused in the sulfonation.

3. A process for the production of aqueous pastes of washing-active α-sulfofatty acid ester salts which, despite high solids contents, are mobile and, in particular, pumpable even at moderately elevated temperatures, said process comprising (1) sulfonating fatty acid alkylesters with sulfur trioxide in molar ratios of up to 1:2, thereby producing crude sulfonic acid, (2) subjecting said sulfonic acid to a post-reaction with at least about 0.5 mole equivalent, based on the sulfur trioxide unused in the sulfonation, of monohydric alcohols and/or alkoxylation products thereof at temperatures above about 70° C., and (3) subsequently working up said sulfonic acid in aqueous medium to obtain α-sulfofatty acid ester salts in a solids content above 35% by weight.

4. A process in accordance with claim 3 wherein said molar ratios are from 1:1.2 to 1:1.8.

5. A process in accordance with claim 3 wherein said post-reaction with said alcohols or alkoxylation products thereof is carried out at temperatures of from about 80° C. to about 100° C., and said alcohols or alkoxylation products thereof are employed in substantially equimolar quantities based on said sulfur trioxide unused in the sulfonation.

6. A process in accordance with claim 3 including working up said sulfonic acid in aqueous medium to obtain α-sulfofatty acid ester salts in a solids content of from about 40 to about 65% by weight.

7. A process in accordance with claim 3 including bleaching said sulfonic acid.

8. A process in accordance with claim 7 wherein said bleaching is performed with an agent selected from hydrogen peroxide and alkali metal hypochlorite.

9. A process in accordance with claim 3 including neutralizing said sulfonic acid to obtain said α-sulfofatty acid ester salt.

10. A process in accordance with claim 3 wherein said post-reaction is performed with monohydric alcohols and/or alkoxylation products thereof containing up to 30 carbon atoms in the alcohol portion, and up to about 20 alkoxy groups in said alkoxylation products.

11. A process in accordance with claim 10 wherein said monohydric alcohols and/or alkoxylation products thereof contain from about 2 to about 22 carbon atoms in the alcohol portion.

12. A process in accordance with claim 10 wherein said alkoxy groups comprise at least about 50% by weight of ethylene oxide groups.

13. A process in accordance with claim 3 wherein said post-reaction is carried out with alkoxylation products of lower alcohols containing up to about 6 carbon atoms, and from about 2 to about 15 ethylene oxide units in the alkoxy group.

14. A process in accordance with claim 3 wherein said post-reaction is carried out with alkoxylation products of lower alcohols containing from about 2 to about 4 carbon atoms, and from about 5 to about 12 ethylene oxide units in the alkoxy group.

15. A process in accordance with claim 3 wherein said post-reaction is carried out with fatty alcohols and/or alkoxylation products thereof containing from about 10 to about 20 carbon atoms.

16. A process in accordance with claim 3 wherein said crude sulfonic acid has a degree of sulfonation of at least about 90% and contains less than about 80 mole % of sulfur trioxide unused in the sulfonation, based on said α-sulfofatty acid ester, when subjected to said post-reaction.

17. A process in accordance with claim 3 wherein said crude sulfonic acid has a degree of sulfonation of at least about 95% and contains less than about 50 mole % of sulfur trioxide unused in the sulfonation, based on said α-sulfofatty acid ester, when subjected to said post-reaction.

18. A process in accordance with claim 3 wherein said aqueous pastes of α-sulfofatty acid ester salts have a disalt content of less than about 10% by weight, based on the weight of said ester salts.

19. A process in accordance with claim 3 wherein no more than about 2 mole equivalents of free alcohol component are used in the post-reaction step.

20. A process in accordance with claim 3 wherein the postreaction step is carried out at temperatures no higher than about 150° C.

* * * * *